United States Patent [19]

Ammann

[11] Patent Number: 5,605,689

[45] Date of Patent: Feb. 25, 1997

[54] TREATMENT OF HIV-ASSOCIATED IMMUNE THROMBOCYTOPENIC PURPURA

[75] Inventor: Arthur J. Ammann, San Rafael, Calif.

[73] Assignee: Genentech, Inc., South San Francisco, Calif.

[21] Appl. No.: 237,962

[22] Filed: May 3, 1994

Related U.S. Application Data

[63] Continuation of Ser. No. 709,006, May 31, 1991, abandoned.

[51] Int. Cl.[6] .................. A61K 39/395; A61K 39/42; A61K 39/44; C07K 16/46
[52] U.S. Cl. .................. 424/134.1; 424/133.1; 424/148.1; 530/387.3; 530/388.35
[58] Field of Search .................. 424/133.1, 134.1, 424/148.1; 435/69.6, 69.7, 70.21, 172.2, 172.3, 240.27, 252.33, 320.1; 530/387.3, 388.35, 389.4

[56] References Cited

U.S. PATENT DOCUMENTS 5,336,603  8/1994  Capon et al. .................. 435/69.7

FOREIGN PATENT DOCUMENTS

| 40173/89 | 3/1990 | Australia . |
|---|---|---|
| 314317 | 5/1989 | European Pat. Off. . |
| 325262 | 7/1989 | European Pat. Off. . |
| 361077 | 4/1990 | European Pat. Off. . |
| 385909 | 9/1990 | European Pat. Off. . |
| 394827 | 10/1990 | European Pat. Off. . |
| WO89/02922 | 10/1988 | WIPO . |
| 90/00617 | 1/1990 | WIPO . |
| WO90/12108 | 10/1990 | WIPO . |

OTHER PUBLICATIONS

Textbook of Immunology, J.T. Barrett, 4th ed. C.V. Mosby Co, St. Louis, pp. 105, 117, 121, 123, 157.
Basch et al. (1990) Proceedings of the National Academy of Sciences, vol. 87, pp. 8085–8089.
Basch et al., "Human Megakaryocytes Have A CD4 Receptor On Their Surface" *Blood* 74(Suppl. 1:206a) :206a (1989).
Chelucci et al., "In Vitro Human Immunodeficiency Virus–1 Infection of Purified Hematopoietic Progenitors in Single–Cell Culture" *Blood* 85(5):1181–1187 (1995).
Matsuo et al., "Characterization of 17 Human Immunodeficiency Virus–1 Carrier Cell Lines with T cell, Myelomoncyte, or Megakaryocyte Lineages (43535)" *P.S.E.B.M.* 202:271 (1993).
Sakaguchi et al., "Human Immunodeficiency Virus Infection of Megakaryocytic Cells" *Blood* 77(3):481–485 (1991).
Zucker–Franklin et al., "Megakaryocytes of human immunodeficiency virus–infected individuals express viral RNA" *Proc. Natl. Acad. Sci.* 86:5595–5599 (1989).
Schafer, A.I. "Thrombocytopenia and Disorders of Platelet Function" in Internal Medicine 3rd Edition, John J. Hutton et al., Eds., Little Brown & Co., Boston/Toronto/London 1990.

Morris et al., "Autoimmune Thrombocytopenic Purpura in Homosexual Men", *Ann. Int. Med.* 96, 714–717 (1982).
Bussel et al., "Intravenous Gammaglobulin Treatment of Chronic Idiopathic Thrombocytopenic Purpura", *Blood* 62(2), 480–486 (1983).
Walsh et al., "On the mechanism of thrombocytopenic purpura in sexually active homosexual men", *N. Engl. J. Med.* 311(10), 635–639 (1984).
Stricker et al., "Target platelet antigen in homosexual men with immune thrombocytopenia", *N. Engl. J. Med.* 313(22), 1375–1380 (1985).
Ratner, L., "Human Immunodeficiency Virus–Associated Autoimmune Thrombocytopenic Purpura: A Review", *Am. J. Med.* 86, 194–198 (1989).
Delfraissy et al., "Intravenous Gammaglobulin, Thrombocytopenia, and the Acquired Immunodeficiency Syndrome", *Ann. Intern. Med.* 103, 478–479 (1985).
J. T. Barrett, *Textbook of Immunology*, 4th Ed., C.V. Mosby Co., St. Louis, pp. 105, 117, 121, 123, 357 (1983).
Panzer et al., "Immune thrombocytopenia in severe hemophilia A treated with high–dose intravenous immunoglubulin", *Transfusion*, 26: 69–72 (1986).
Basch et al., "Expression of CD4 by human megakaryocytes", *Proc. Natl. Acad. Sci.*, 87: 8085–8089 (1990).
Ordi et al., "Serum Thrombocytopenia and High–Dose Immunoglobulin Treatment", *Ann. Intern. Med.* 104, 282–283 (1986).
Oksenhendler et al., "Anti–RH Immunoglobulin Therapy for Human Immunodeficiency Virus–Related Immune Thrombocytopenic Purpura", *Blood* 71(5), 1499–1502 (1988).
Bierling et al., "Anti–Rhesus Antibodies, Immune Thrombocytopenia, and Human Immunodeficiency Virus Infection", *Ann. Intern. Med.* 106, 773–774 (1987).
Biniek et al., "Anti–Rh(D) immunoglobulin for AIDS–related thrombocytopenia", *Lancet* 2, 627 (1986).
Abrams, D.I. "HIV–Related Immune Thrombocytopenic Purpura" in The AIDS Knowledge Base, Cohen, P.T. et al., Eds., The Medical Publishing Group, Waltham, Massachusetts, (1990).
IGIV Bulletin, Highlights from the 1990 NIH Consensus Development Conference, Bethesda, MD, May 21–23, 1990.
Lohmann et al., "Idiopathic thrombocytopenia treated with PAF–acether antagonist web 2086", *Lancet* 1147 (1988).
Oksenhendler et al., "HIV–Related Immune Thrombocytopenia: Follow–up and Treatment of 157 Patients", *6th Int. Conf. on AIDS*, 20–22 Jun. 1990, San Francisco, CA, Abstracts vol. 2, p. 207 F.B. 519.

(List continued on next page.)

*Primary Examiner*—Robert D. Budens
*Attorney, Agent, or Firm*—Jeffrey S. Kubinec

[57]  ABSTRACT

The invention relates to a method for treating HIV-associated immune thrombocytopenic purpura (ITP) which comprises administering to a patient in need of such treatment a therapeutically effective amount of a molecule comprising an amino acid sequence capable of binding to HIV.

7 Claims, 3 Drawing Sheets

OTHER PUBLICATIONS

Cinque et al., "Medium–long term efficacy of zidovudine in HIV–related thrombocytopenia", *6th Int. Conf. on AIDS*, 20–22 Jun. 1990, San Francisco, CA, Abstracts vol. 2, p. 208 F.B. 520.

Santagostino et al., "Anti–D immunoglobulin for treatment of immune thrombocytopenic purpura (ITP): Comparison between HIV–related ITP and idiopathic ITP", *6th Int. Conf. on AIDS*, 20–22 Jun. 1990, San Francisco, CA, Abstracts vol. 2, p. 208F.B. 521.

Rossi et al., "Effectiveness of a short–course of recombinant alpha–2b interferon therapy for severe HIV–related thrombocytopenia (TP)", *VIIth Int. Conf. on AIDS*, 16–21 Jun. 1991, Florence, Italy, p. 269, M.B. 2351.

Richman et al., "The toxicity of azidothymidine (AZT) in the treatment of patients with AIDS and AIDS–related complex", *J. Engl. J. Med.* 317, 192–197 (1987)..

Fischl et al., "The efficacy of azidothymidine (AZT) in the treatment of patients with AIDS and AIDS–related complex", *N. Engl. J. Med.* 317, 185–191 (1987).

Gascoigne et al., "Secretion of a chimeric T–cell receptor–immunoglobulin protein", *Proc. Natl. Acad. Sci. USA* 84, 2936–2940 (1987).

Nydegger, U.E. et al., "Review on therapeutic options in HIV associated thrombocytopenia with emphasis on I. V. immunoglobulin treatment", *Immunol. Investigations* 20: 223–229 (1991).

Hirschel et al., "Zidovudine for the Treatment of Thrombocytopenia Associated with Human Immunodeficiency Virus (HIV)", *Ann. Intern. Med.* 109, 718–721 (1988).

Brusamolino et al., "HIV–Related Thrombocytopenic Purpura: A Study of 24 Cases", *Haematological* 74, 51–56 (1989).

Karpatkin et al., "Anti–human immunodeficiency virus type 1 antibody complexes on platelets of seropositive thrombocytopenic homosexuals and narcotic addicts", *Proc. Natl. Acad. Sci. USA* 85, 9763–9767 (1988).

Giuseppe et al., "Thrombocytopenia in HIV Infection", *Vth Int. Conf. on AIDS*, Montreal, Quebec, Canada, Jun. 4–9, 1989, p. 331, Abstract T.B.P. 269.

Ballem, Penny et al., "Platelet production in HIV infection—evidence for a compensated thrombolytic state enhanced by AZT", *Vth Int. Conf. on AIDS*, Montreal, Quebec, Canada, Jun. 4–9, 1989, p. 332, Abstract T.B.P. 270.

Flegg et al., "Effects of long term zidovudine on platelet count", *Vth Int. Conf. on AIDS*, Montreal, Quebec, Canada, Jun. 4–9, 1989, p. 332, Abstract T.B.P. 271.

Landoruo et al., "Response to splenectomy for severe HIV–related thrombocytopenia in 10 drug abusers and pathological features of the spleen", *Vth Int. Conf. on AIDS*, Montreal, Quebec, Canada, Jun. 4–9, 1989, p. 332, Abstract T.B.P. 272.

Oksenhendler et al., "HIV–Related Immune Thrombocytopenia: Follow–up and Treatment of 132 Patients", *Vth Int. Conf. on AIDS*, Montreal, Quebec, Canada, Jun. 4–9, 1989, p. 332, Abstract T.B.P. 273.

Cárcaba et al., "HIV–associated thrombocytopenia (HIP) platelet–associated immunoglobulin (PAI) and zidovudine", *Vth Int. Conf. on AIDS*, Montreal, Quebec, Canada, Jun. 4–9, 1989, p. 332, Abstract T.B.P. 274.

Gee et al., "Therapy of HIV Associated Thrombocytopenia", *Vth Int. Conf. on AIDS*, Montreal, Quebec, Canada, Jun. 4–9, 1989, p. 333, Abstract T.B.P. 275.

Scolaro et al., "Lack of efficacy of on–line column–A–adsorption in treatment of HIV–associated ITP", *Vth Int. Conf. on AIDS*, Montreal, Quebec, Canada, Jun. 4–9, 1989, p. 333, Abstract T.B.P. 276.

Routy et al., "Efficacite de la zidovudine a faible dose dans le traitment des thrombopenies liees au virus HIV", *Vth Int. conf. on AIDS*, Montreal, Quebec, Canada, Jun. 4–9, 1989, p. 333, Abstract T.B.P. 277.

Arrizobologa et al., "Combined steroid–zidovudine treatment of severe thrombocytopenia asssociated with HIV infection", *Vth Int. Conf. on AIDS*, Montreal, Quebec, Canada, Jun. 4–9, 1989, p. 333, Abstract T.B.P. 278.

Luzzati et al., "Alpha–interferon in treatment of severe HIV–related thrombocytopenia (TP)", *6th Int. Conf. on AIDS*, 20–22 Jun. 1990, San Francisco, CA, Abstracts vol. 2 p. 206 F.B. 512.

Lacoste et al., "Is HIV–associated thrombocytopenia a prognosis factor for AIDS? Hospital–based surveillance, Bordeaux, France, 1985–1989", *6th Int. Conf. on AIDS*, 20–22 Jun. 1990, San Francisco, CA, Abstracts vol. 2 p. 206 F.B. 513.

Church et al., "HIV–associated thrombocytopenia (HAPT) in children", *6th Int. Conf. on AIDS*, 20–22 Jun. 1990, San Francisco, CA, Abstracts vol. 2 p. 206 F.B. 514.

Landonio et al., "HIV–related thrombocytopenia includes various forms of thrombocytopenias", *6th Int. Conf. on AIDS*, 20–22 Jun. 1990, San Francisco, CA, Abstracts vol. 2 p. 206 F.B. 515.

Dominguez et al., "Response to therapy in 31 patients with HIB–related thrombocytopenia", *6th Int. Conf. on AIDS*, 20–22 Jun. 1990, San Francisco, CA, Abstracts vol. 2 p. 207 F.B. 516.

Carton et al., "Efficacy of zidovudine in the treatment of HIV infection associated thrombocytopenia", *6th Int. Conf. on AIDS*, 20–22 Jun. 1990, San Francisco, CA, Abstracts vol. 2 p. 207 F.B. 517.

Drenaggi et al., "Antiplatelet antibodies in HIV infection", 6th Int. Conf. on AIDS, 20–22 Jun. 1990, San Francisco, CA, Abstracts vol. 2 p. 207 F.B. 518.

Capon et al., "Designing CD4 immunoadhesins for AIDS therapy", *Nature* 337, 525–531 (1989).

Traunecker et al., "Highly efficient neutralization of HIV with recombinant CD4–immunoglobulin molecules", *Nature* 339, 68–70 (1989).

Byrn et al., "Biological properties of a CD4 immunoadhesin", *Nature* 344, 667–670 (1990).

Kahn et al., "The Safety and Pharmacokinetics of Recombinant Soluble CD4(rCD4) in Subject with the Acquired Immunodeficiency Syndrome (AIDS) and AIDS–Related Complex", *Ann. Int. Med.* 112(4), 254–261 (1990).

Ezzel, C. "AIDS closer to becoming a treatable disease", *Nature* 340, 581 (1989).

Chamow et al., "Enzymatic Cleavage of a CD4 Immunoadhesin Generates Crystallizable, Biologically Active Fd–like Fragments", *Biochemistry* 29(42), 9885–9891 (1990).

Capon et al., "Biological properties of CD4 immunoadhesions", *6th Int. Conf. on AIDS*, 20–22 Jun. 1990, San Francisco, CA, Abtracts, vol. 2, p. 153 Th.A.80.

Berg et al., "Immunoadhesion–antibody hybrids for AIDS therapy", *6th Int. Conf. on AIDS*, 20–22 Jun. 1990, San Francisco, CA, Abstracts, vol. 2, p. 178 Th.A. 234.

Potts et al., "The interaction of recombinant soluble CD4 (sT4) and GP120 in normal human and AIDS patient plasma", *6th Int. Conf. on AIDS*, 20–22 Jun. 1990, San Francisco, CA, Abstracts, vol. 2, p. 182 Th.A. 250.

Crysler et al., "Whole blood distribution and quantitation of recombinant soluble CD4 (sT4) in HIV–infected plasma by single and double monoclonal based ELISAs directed to sT4 V1 and V4 regions", *6th Int. Conf. on AIDS*, 20–22 Jun. 1990, San Francisco, CA, Abstracts, vol. 2, p. 182 Th.A. 251.

Hodges et al., "Phase I study of the safety and pharmokinetics of recombinant human CD4 immunoglobulin (rCD4–IgG) administered by intramuscular (IM) injection in patients with AIDS and ARC", *6th Int. Conf. on AIDS*, 20–22 Jun. 1990, San Francisco, CA, Abstracts, vol. 3, p. 205 S.B. 478.

Yarchoan et al., "Phase I study of rCD4–IgG administered by continuous intravenous (IV) infusion to patients with AIDS or ARC", *6th Int. Conf. on AIDS*, 20–22 Jun. 1990, San Francisco, CA, Abstracts, vol. 3, p. 205 S.B. 479.

Collier et al., "Safety and pharmakinetics of intravenous recombinant CD4 immunoadhesion (RCDD–IGG) (AIDS" *6th Int. Conf. on AIDS*, 20–22 Jun. 1990, San Francisco, CA, Abstracts, vol. 3, p. 206, S.B. 480.

Davey et al., "A Phase I trial of recombinant human CD4–immunoglobulin (rCD4–IgG) in HIV–1 infection", *6th Int. Conf. on AIDS*, 20–22 Jun. 1990, San Francisco, CA, Abstracts, vol. 3, p. 205 S.B. 481.

Nydegger, U.E. et al., *Immunol. Investigations* 20: 223–229 (1991).

Giuseppe et al., Vth Int. Conf. on AIDS, Montreal, Quebec, Canada, Jun. 4–9, 1989 Abstract T.B.P. 269.

Penny et al., Vth Int. Conf. on AIDS, Montreal, Quebec, Canada, Jun. 4–9, 1989, Abstract T.B.P. 270.

Flegg et al., Vth Int. Conf. on AIDS, Montreal, Quebec, Canada, Jun. 4–9, 1989, Abstract T.B.P. 271.

Landoruo et al., Vth Int. Conf. on AIDS, Montreal, Quebec, Canada, Jun. 4–9, 1989, Abstract T.B.P. 272.

Oksenhandler et al., Vth Int. conf. on AIDS, Montreal, Quebec, Canada, Jun. 4–9, 1989, Abstract T.B.P. 273.

Vincente et al, Vth Int. conf. on AIDS, Montreal, Quebec, Canada, Jun. 4–9, 1989, Abstract T.B.P. 274.

Gee et al., Vth Int. conf. on AIDS, Montreal, Quebec, Canada, Jun. 4–9, 1989, Abstract T.B.P. 275.

Scolaro et al., Vth Int. conf. on AIDS, Montreal, Quebec, Canada, Jun. 4–9, 1989, Abstract T.B.P. 276.

Routy et al., Vth Int. conf. on AIDS, Montreal, Quebec, Canada, Jun. 4–9, 1989, Abstract T.B.P. 277.

Arrizobologa et al., Vth Int. conf. on AIDS, Montreal, Quebec, Canada, Jun. 4–9, 1989, Abstract T.B.P. 278.

de Stuotz et al., sixth Int. Conf. on AIDS, 20–22 Jun. 1990, San Francisco, CA, Abstracts vol. 2, p. 205 F.B. 511.

TREATMENT OF HIV-ASSOCIATED IMMUNE THROMBOCYTOPENIC PURPURA

This is a continuation of application Ser. No. 07/709,006 filed on 31 May 1991, now abandoned.

FIELD OF THE INVENTION

This application relates to the treatment of human immunodeficiency virus (HIV)-associated Immune Thrombocytopenic Purpura (ITP).

BACKGROUND OF THE INVENTION

Thrombocytopenia is defined as a platelet count below $150 \times 10^9$ per liter, and can be due to a number of different disorders, including, for example, impaired production of platelets by the bone marrow, platelet sequestration due to splenomegaly, or increased destruction of platelets in the peripheral circulation. Based upon their underlying cause, the throbocytopenias can be divided into different categories [Schaefer, A. I., "Thrombocytopenia and Disorders of Platelet Function" pp. 1041–1049 in Internal Medicine, 3rd Edition, John J. Hutton et al., Eds., Little Brown and Co., Boston/Toronto/London, 1990]. One of these categories, immune (autoimmune) thrombocytopenic purpura (ITP) is an uncommon illness caused by the production of antibodies to platelets and the subsequent destruction of platelets by the reticuloendothelial system. The autoantibody is usually IgG although other immunoglobulins have also been reported. The clinical bleeding manifestations of ITP depend on the severity of the condition, and possible associated coagulation effects. In severe cases, bleeding can be life threatening [Morris et al., Ann. Int. Med. 96, 714–717 (1982)]. Chronic ITP is usually accompanied by increased megakaryocytes in the bone marrow and frequently by an elevated platelet-associated immunoglobulin G (PAIgG) [Bussel et al., Blood 62-2, 480–486 (1983)].

ITP is also a common complication of HIV infection [Morris et al., Ann. Intern. Med. 96,714–717 (1982)], which can occur at any stage of its natural history, both in patients diagnosed with the Acquired Immune Deficiency Syndrome (AIDS), those with AIDS-related complex, and those with HIV infection but without AIDS symptoms.

AIDS is a transmissible disease characterized by a profound deficiency of cellular immune function and the occurrence of opportunistic infection and malignancy. In 1983, a retrovirus was identified in association with this syndrome [Barre-Sinoussi, F., Chermann, J. C., Rey, F. et al., Science 220, 868–871 (1983); and Gallo, R. C., Salahuddin, S. Z., Popovic, M., et al., Science 224, 500–503 (1984)]. Subsequently, there have been numerous isolations of related retroviruses from patients in different geographical areas, and the etiologic role of this retrovirus has been clearly established. Whereas initially these isolates were variously referred to as lymphadenopathy associated virus (LAV), human T cell lymphotropic virus-III (HTLV-III) or AIDS associated retrovirus (ARV), today the accepted terminology is human immunodeficiency virus (HIV), which has more subtypes, e.g. HIV type-1 (HIV-I) and HIV type-2 (HIV-2).

The primary immunologic abnormality resulting from infection by HIV is the progressive depletion and functional impairment of T lymphocytes expressing the CD4 cell surface glycoprotein (H. Lane et al., Ann. Rev. Immunol. 3:477 [1985]). CD4 is a nonpolymorphic glycoprotein with homology to the immunoglobulin gene superfamily (P. Maddon et al., Cell 42:93 [1985]). Together with the CD8 surface antigen, CD4 defines two distinct subsets of mature peripheral T cells (E. Reinherz et al., Cell 19:821 [1980]), which are distinguished by their ability to interact with nominal antigen targets in the context of class I and class II major histocompatibility complex (MHC) antigens, respectively (S. Swain, Proc. Natl. Acad. Sci. 78:7101 [1981]; E. Engleman et al., J. Immunol. 127:2124 [1981]; H. Spitz et al., J. Immunol. 129:1563 [1982]; W. Biddison et al., J. Exp. Med. 156:1065 [1982]; and D. Wilde et al., J. Immunol. 131:2178 [1983]). For the most part, CD4 T cells display the helper/inducer T cell phenotype (E. Reinherz, supra), although CD4 T cells characterized as cytotoxic/suppressor T cells have also been identified (Y. Thomas et al., J. Exp. Med. 154:459 [1981]; S. Meuer et al., Proc. Natl. Acad. Sci. USA 79:4395 [1982]; and A. Krensky et al., Proc. Natl. Acad. Sci. USA 79:2365 [1982]). The loss of CD4 helper/inducer T cell function probably underlies the profound defects in cellular and humoral immunity leading to the opportunistic infections and malignancies characteristic of AIDS (H. Lane supra).

The clinical spectrum of HIV infection is very complex, and the current therapy is directed toward the underlying retroviral infection as well as towards the specific opportunistic infections and malignancies that are associated with the syndrome.

Although the mechanism of HIV-associated ITP is unknown, it is believed to be different from the mechanism of ITP not associated with HIV infection in more characteristics.

In a study by Walsh et al. [N. Engl. J. Med. 311, 635–639 (1984)]ITP in 33 homosexual men who were presumed to be HIV-positive, was compared with non-HIV-related chronic ITP in 15 women and eight men. Individuals with HIV-associated ITP were reported to have 3.8-fold higher levels of platelet associated IgG and 4.2-fold higher levels of platelet-associated complement than did the patients with non-HIV-related ITP. Platelet eluates from 12 of 15 patients with non-HIV-related ITP bound platelets at a mean dilution titer of 1:8, whereas those from only one of the 10 individuals with HIV-associated ITP bound platelets at a titer of 1:2. Also, IgG in the serum of three patients with HIV-associated ITP was not capable of binding platelets, whereas IgG from two patients with non-HIV-associated ITP could bind platelets. Circulating immune complexes (CICs) were detected by the polyethylene glycol precipitation method in 88% of the individuals having HIV-associated ITP, and in 79% the CICs were capable of binding to platelets. CICs were not found in any of five patients with non-HIV-associated ITP. These and similar findings have led to the hypothesis that HIV-related ITP results from the deposition of immune complexes and complement on platelets. The immune complex deposition occurs on platelet Fc receptors. Monocytes or macrophages would then bind to free Fc domains of exposed IgG molecules or to platelet-bound complement by the C3b receptors.

An alternative hypothesis is that HIV-associated ITP results from an autoimmune process associated with the presence of a serum antibody that binds to a target platelet antigen of 25,000 kilodaltons (kD). There is a suggestion that the 25 kD protein resembles part of a sequence from the HIV polypeptide. Molecular mimicry between HIV and platelet antigens may play a role in the induction of ITP in HIV-infected individuals. This hypothesis is essentially based on a study by Stricker et al., N. Engl. J. Med. 313, 1375–1380 (1985). The authors studied ITP in patients including 30 homosexual men, 18 non-homosexual individuals with ITP, 12 patients with nonimmune thrombocytopenia and 16 homosexual men with normal platelet counts diagnosed to have either AIDS-related complex (ARC) or AIDS. Using a sensitive immunoblot technique, an antibody was identified in the sera of 9 of 30 patients with HIV-associated ITP that bound to a 25 kilodalton antigen on platelets. This activity was not found in the sera of patients with non-HIV-associated ITP or nonimmune thrombocytopenia. The serum binding activity for the 25 kilodalton platelet antigen was found in the IgG fraction and was mediated by the F(ab)$_2$ fragment.

For further details, I refer to a recent review article by Ratner, L., [*Am. J. Med.* 86, 194–198 (1989)], and the references cited therein.

The therapeutic approach to the treatment of patients with ITP is dictated by the severity and urgency of the clinical situation. The treatment is similar for HIV-associated and non-HIV-related ITP, and although a number of different therapeutic approaches have been used in the clinical practice, the therapy remains controversial.

In many adult patients with (HIV-associated) ITP thrombocytopenia is mild (the platelet count is more than about 20–30×10$^9$/liter) and no bleeding occurs. In such cases monitoring with no therapy is considered to be the best option.

Platelet counts in patients diagnosed with ITP have been successfully increased by glucocorticoid (e.g. prednisolone) therapy, however in most patients the response is incomplete, or relapse occurs when the glucocorticoid dose is reduced or its administration is discontinued. Based upon studies with patients having HIV-associated ITP, some investigators have suggested that glucocorticoids may predispose to AIDS. This approach is usually followed if the platelet count is below 20×10$^9$/liter or if bleeding occurs.

Good results were reported with splenectomy. Splenectomy removes the major site of platelet destruction and a major source of autoantibody production in many patients. This procedure results in prolonged treatment-free remissions in a large number of patients. However, since surgical procedures are generally to be avoided in immune compromised patients, splenectomy is recommended in severe cases of HIV-associated ITP only, in patients who fail to respond to 2 to 3 weeks of glucocorticoid treatment, or do not achieve sustained response after discontinuation of glycocorticoid administration. Based upon current scientific knowledge, it is unclear whether splenectomy predisposes patients to AIDS.

Significant responses have been documented to high doses (about 500 mg/kg body weight and above) of immunoglobulin [Rarick et al., Proceedings of the Fourth International Conference on AIDS, Stockholm, (1988) p. 7642; Sanderson et al., *ibid*, p. 7646; Panzer et al., *Transfusion* 26, 69–72 (1986); Delfraissy et al., *Ann. Intern. Med.* 103, 478–479 (1985); Ordi et al., *Ann. Intern Med.* 104, 282–283 (1986)], and to anti-Rh immunoglobulin treatment [Oksendhendler et al., *Blood* 71, 1499–1502 (1988); Bierling et al., *Ann. Intern. Med.* 106, 773–774 (1987); Durand et al., *Lancet* 2:40 (1986); Biniek et al., Lancet 2:627 (1986)].

Certain cytotoxic agents, e.g. vincristine, and azidothimidine (AZT, zidovudine) have also shown some promising effects, however, the results are very preliminary.

AZT, a reverse transcriptase inhibitor nucleoside analogue, has been extensively tested in AIDS therapy and was found to result in a decreased incidence of opportunistic infections and increased survival in AIDS patients [Fischl et al., *N. Engl. J. Med.* 317, 185–191 (1987)]. However, it is clear that AZT therapy is associated with significant dose-limiting toxicities, including anemia and other hematologic toxicity, particularly in individuals with advanced HIV infection [Richman et al., *N. Engl. J. Med.* 317, 192–197 (1987)]. Similarly, the toxicity of cytotoxic agents, such as vincristine is of great concern.

CD4-Immunoglobulin hybrid molecules are known in the art, and are, for example, disclosed in co-pending U.S. application Ser. No. 07/250,785 (filed 28 Sep. 1988), which is a continuation-in-part of Serial No. 07/104,329 (filed 2 Oct. 1987), and in the counterpart PCT Application Publication No. WO 89/02922 (published 6 Apr. 1989). Fusion proteins of immunoglobulins of the IgM, IgG1 or IgG3 class, wherein the variable region of the light or heavy chain has been replaced with CD4 or CD4 fragments are also described in EP 325,262. Such fusion proteins have so far been recommended for the treatment of HIV infection or for use in assays for detection of the HIV virus. According to WO 89/02922 the typical dose for the treatment of HIV infection corresponds to about 100 μg/kg/day soluble CD4. According to EP 325,262 the dose of the CD4-immunglobulin molecule may vary from 0.01 mg/kg to 50 mg/kg, 0.1 mg/kg to 1.0 mg/kg being preferred.

The results of a phase 1 clinical study initiated to evaluate the safety and pharmacokinetics of a recombinant soluble CD4 (rCD4) molecule in the treatment of AIDS were reported by Kahn et al. in *Annals of Internal Medicine* 112(4), 254–261 (1990). The patients were enrolled at dose levels of 1, 10, 30, 100, and 300 μg/kg body weight of rCD4 administered intravenously. One of the patients had a platelet count of 68×10$^9$/liter at entry, and during the rCD4 treatment had a progressive decrease to 41×10$^9$/liter at the time that disseminated histoplasmosis with bone marrow involvement was diagnosed.

It is an object of the present invention to provide an efficient treatment for HIV-associated ITP which is devoid of the disadvantages of the hitherto known approaches.

SUMMARY OF THE INVENTION

The object of the present invention is accomplished by providing a method for treating HIV-associated immune thrombocytopenic purpura (ITP) which comprises administering to a patient in need of such treatment a therapeutically effective amount of a molecule comprising an amino acid sequence capable of binding to HIV.

In a further aspect, the present invention concerns a method for treating HIV-associated ITP which comprises:

a) administering to a patient having the condition of HIV-associated ITP a therapeutically effective amount of a molecule comprising an amino acid sequence capable of binding to HIV;

b) monitoring the change in a parameter or symptom characteristic of the condition of HIV-associated ITP in response to the administration; and c) continuing the treatment until a positive response is attained.

The amino acid sequence capable of binding to HIV may, for example, be a CD4 or an immunoglobulin variable domain sequence, optionally fused to a carrier amino acid sequence which is preferably an immunoglobulin constant domain sequence.

According to a particular embodiment, the treatment is performed with a hybrid molecule comprising a CD4 sequence which is capable of binding to HIV, said sequence being fused to an immunoglobulin constant domain sequence. Typically, the CD4 sequence is a portion of the extracellular domain of the CD4 receptor. The immunoglobulin sequence may be obtained from IgG-1, -2, -3, or -4 subtypes, IgA, IgE, IgD or IgM, and preferably is a portion of human immunoglobulin of the IgG-1 subclass.

In another embodiment, anti-HIV monoclonal antibodies are used in the above method.

DETAILED DESCRIPTION

Figure 1:
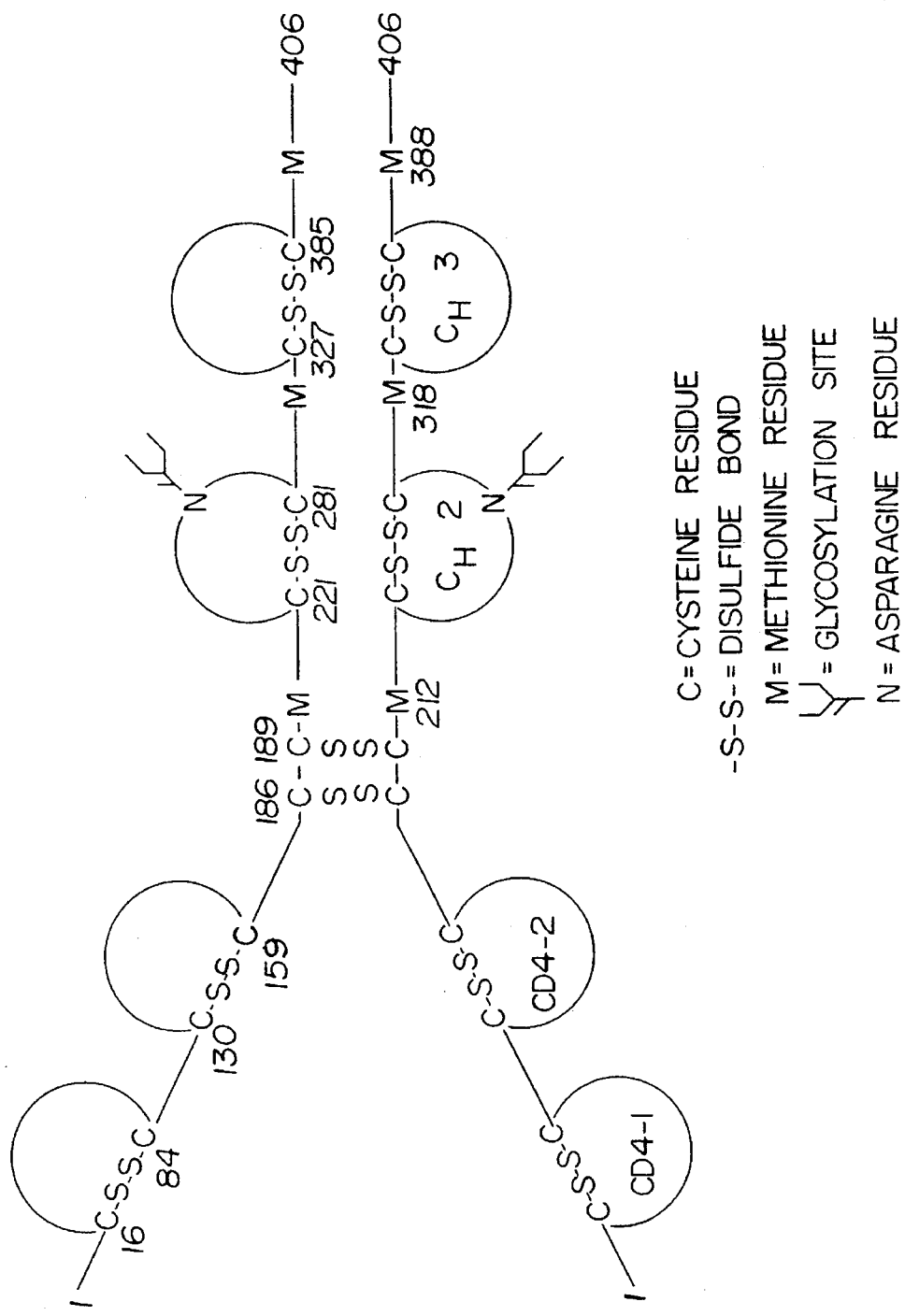
FIG. 1 illustrates the structure of the human soluble recombinant CD4-immunoglobulin (rCD4-IgG-1) hybrid molecule used in the example.

HIV is a retrovirus, containing three regions encoding structural proteins. The gag region encodes the core proteins of the virion, the pol region encodes the virion reverse transcriptase, and the env region encodes the major glycoprotein found in the membrane envelope of the virus and in the cytoplasmic membrane of the cells infected with the HIV virus. The structural element which is believed to play a fundamental role in the pathogenesis of the virus is the env region encoding a precursor env (envelope) polypeptide gp160. Cleavage of this precursor yields gp120 (a heavily glycosylated exterior membrane protein of about 481 amino acids) and gp41 (a transmembrane protein of about 345 amino acids). For further details about the structure and complete nucleotide sequence of HIV see, e.g. Ratner et al., Nature 313, 277–285 (1985).

Molecules comprising an amino acid sequence capable of binding to any domain within the env region including the gp160, gp120 and gp41 regions, are all contemplated as being useful for the purpose of the present invention.

A molecule known to bind to gp120 is the cell surface glycoprotein, CD4.

The known sequence of the CD4 precursor predicts a hydrophobic signal peptide, an extracellular region of approximately 370 amino acids, a highly hydrophobic stretch with significant identity to the membrane-spanning domain of the class II MHC beta chain, and a highly charged intracellular sequence of 40 residues [P. Maddon, Cell 42, 93 (1985)]. Because of its amino acid sequence homology with immunoglobulin polypeptide chains, CD4 is considered to be a member of the immunoglobulin gene superfamily.

Detailed molecular studies of the CD4 molecule indicate that it is a transmembrane protein. The extracellular domain of CD4 consists of four contiguous regions each having amino acid and structural similarity to the variable and joining (V-J) domains of immunoglobulin light chain as well as related regions in other members of the immunglobulin gene superfamily. These structurally similar regions of CD4 are termed the V1, V2, V3 and V4 domains. The boundaries for the CD4 V-like regions (V1–V4) are, respectively, about 100–109, about 175–184, about 289–298, and about 360–369, based on the precursor CD4 amino acid sequence in which the initiating met is −25, as disclosed by Arthos et al., Cell 57, 469 (1989).

Truncation studies of the CD4 molecule have been conducted to identify the region to which the viral gp 120 actually binds. Results of these studies suggest that the V1 region, consisting of approximately the first 100 amino acids of the extracellular domain, is alone sufficient for binding of gp 120 [Richardson et al., Proc. Nat'l. Acad. Sci. USA 85, 9273 (1988); Landau et al., Nature 334, 159 (1988)]. Several approaches have been used to define the amino acids within the V1 region to which gp 120 binds. These approaches include the techniques of random saturation mutagenesis coupled with selection of escape mutants [Peterson and Seed, Cell 54, 65 (1988) and EP 342,444 A2 published 15 Nov. 1989]; insertional mutagenesis [Mizukami et al., Proc. Nat'l. Acad. Sci. USA 85, 9273 (1988)]; homolog-scanning mutagenesis (replacement of sequences from human CD4 which binds gp 120, with unconserved sequences from mouse CD4, which does not bind gp 120) [Landau et al., Nature 334, 159 (1988); Clayton et al., Nature 335, 363 (1988); WO 89/0322, published 20 Apr. 1989; and Brodsky et al., J. Immunol. 144, 3078 (1990)]; and alanine scanning mutagenesis [Ashkenazi et al., Proc. Nat'l. Acad. Sci. USA 87, 7150 (1990)].

The term "CD4" in the context of the present invention is used to refer to a polypeptide comprising the sequence of the native human CD4 molecule as disclosed by Arthos et al., Supra, or any derivative or fragment thereof which is effective in the treatment of ITP. This definition includes CD4 polypeptides from natural source, synthetically produced or obtained by genetic manipulation including methods of recombinant DNA technology, and specifically encompasses the sequence initially published by Maddon et al., Supra, which indicates an asparagine residue (codon AAC) at the 26 position (position 1 of mature CD4), although it has later been found that the sequence which occurs in nature contains a lysine residue at this position (encoded by AAG). "CD4 derivatives" as defined for the purpose of the present invention, specifically include CD4 molecules having the qualitative gp 120 binding characteristics of native human CD4 and comprising a gp 120 binding domain of CD4. This definition includes alleles, fragments (truncated versions) and insertional and deletional sequence variants of native CD4 (see co-pending U.S. application Ser. No. 07/512,691 filed 23 Apr. 1990). In a particular group of such CD4 derivatives at least the transmembrane domain is inactivated so that it is incapable of cell membrane insertion. This is typically accomplished by deletion of the transmembrane domain, optionally including deletion of the cytoplasmic domain and all extracellular sequence located downstream from the first two variable region-like domains of CD4. The CD4 polypeptides are lysine N-terminal (the native sequence) or are N-terminated by asparagine or other suitable residues in place of lysine. CD4 derivatives are, for example disclosed in the U.S. Application Serial No. 07/104, 399 filed 26 Oct. 1987 (now abandoned), its Continuation-In-Part Ser. No. 07/250,785 filed 28 Sep. 1988 (PCT WO 89/02922, published 6 Apr. 1989), its Continuation-In-Part Ser. No. 07/275,296 filed 23 Nov. 1988 (PCT WO 90/05534, published 31 May 1990) and its Continuation-In-Part Ser. No. 07/512,691 filed 23 Apr. 1990. Further CD4 derivatives which qualify for the purpose of the present invention are easily identified by using the test method disclosed in the Example of the present application.

CD4 is a glycoprotein, which is defined as a polypeptide comprising a carbohydrate substituent. In glycoproteins, the carbohydrate typically is a branched polysaccharide containing fucose, N-acetylglucosamine, galactose, mannose, Nacetylneuraminic acid (sialic acid) and other sugar residues. The carbohydrate is substituted at N-linked glycosylation sites (asp X thr/ser, where X is any residue) or, in other polypeptides, at O-linked sites (typically serine) or at both O and N-linked sites. It will be understood that CD4 from other recombinant hosts may contain different sugars or may vary in the relative proportions of the sugars shown above. It is within the scope hereof to move, add or delete glycosylation sites by site-directed mutagenesis of CD4 polypeptide either used alone or as a component of the CD4-immunoglobulin hybrids, in order to modify their properties.

According to a preferred embodiment of the invention, CD4 is conjugated to an immunoglobulin (Ig) constant domain to yield CD4-immunoglobulin hybrid molecules. Such molecules have a longer half-life and lower clearance than CD4 molecules alone, producing much higher steady-state CD4 concentrations for equivalent doses [Capon et al., *Nature* 337, 525–531 (1989)].

Immunoglobulins and certain variants thereof are known and many have been prepared in recombinant cell culture. For example, see U.S. Pat. No. 4,745,055; EP 256,654; Faulkner et al., *Nature* 298:286 (1982); EP 120,694; EP 125,023; Morrison, *J. Immun.* 123:793 (1979); Köhler et al., *Proc. Nat'l. Acad. Sci. USA* 77:2197 (1980); Raso et al., *Cancer Res.* 41:2073 (1981); Morrison et al., *Ann. Rev. Immunol.* 2:239 (1984); Morrison, *Science* 229:1202 (1985); Morrison et al., *Proc. Nat'l. Acad. Sci. USA* 81:6851 (1984); EP 255,694; EP 266,663; and WO 88/03559. Reassorted immunoglobulin chains also are known. See for example U.S. Pat. No. 4,444,878; WO 88/03565; and EP 68,763 and references cited therein.

The term "CD4-immunglobulin hybrid" and grammatical variants thereof as defined for the purpose of the present invention refer to molecules comprising a CD4 moiety as hereinabove defined conjugated to an immunglobulin constant domain. Ordinarily, the CD4 moiety is linked at its C-terminus to the N-terminus of the constant region of an immunoglobulin in place of the variable region(s) thereof, retaining at least the CH2 and CH3 domains of the constant region of an immunoglobulin heavy chain and preferably, a functionally active hinge. This ordinarily is accomplished by constructing the appropriate DNA sequence and expressing it in recombinant cell culture.

In a specific group, a CD4 sequence containing the CD4 HIV-binding V-like regions is fused to the immunoglobulin sequence. It is preferable that the V1, V1V2 or V1V2V3V4 regions be fused at their C-termini to the N-terminus of an immunoglobulin constant region. The precise site at which the fusion is made is not critical; the boundary domains noted herein are for guidance only and other sites neighboring or within the V regions may be selected in order to optimize the secretion or binding characteristics. The optimal site can be determined by routine experimentation. In general, it has been found that the fusions are expressed intracellularly, but a great deal of variation is encountered in the degree of secretion of the fusions from recombinant hosts. The following table demonstrates a number of various immunoglobulin fusions that have been made as examples of structures that are believed to be suitable for the purpose of the present invention. In all examples, the CD4 signal was used to direct secretion from 293 cells. Lower case m represents murine origin, while the lower case h designates human origin. V and C are abbreviations for immunoglobulin variable and constant domains respectively. The numerical subscripts indicate the number of parenthetical units found in the designated multimer. It will be understood that the chains of the multimers are believed to be disulfide bonded in the same fashion as native immunoglobulins. The CD4 immunoglobulin hybrids typically contain either the first N-terminal 366 residues of CD4 ($CD4_4$) or the first 180 N-terminal residues of CD4 ($CD4_2$) linked at their C-terminus to the κ (light) chain or IgG-1 heavy chain constant region (γ1).

TABLE I

| Transfected Gene | Secreted Product |
|---|---|
| $hCD4\text{-}mC_\kappa$ | $hCD4\text{-}mC_\kappa$ and/or $(hCD4\text{-}mC_\kappa)_2$ |
| $hCD4\text{-}mC_\kappa + hCD4\text{-}mC_{\gamma 1}$ | $(hCD4\text{-}mC_\kappa)_2(hCD4\text{-}mC_{\gamma 1})_2 +$ $hCD4\text{-}mC_\kappa$ and/or $(hCD4\text{-}mC_\kappa)_2$ |
| $hCD4\text{-}hC_\kappa$ | $hCD4\text{-}hC_\kappa$ and/or $(hCD4\text{-}hC_\kappa)_2$ |
| $hCD4\text{-}hC_{\gamma 1}$ | $(hCD4\text{-}hC_{\gamma 1})_2$ |
| $hCD4\text{-}hC_\kappa + hCD4\text{-}hC_{\gamma 1}$ | $(hCD4\text{-}hC_\kappa)_2(hCD4\text{-}hC_{\gamma 1})_2 +$ $hCD4\text{-}hC_\kappa$ and/or $(hCD4\text{-}hC_\kappa)_2$ |
| $mV_\kappa C_\kappa + hCD4\text{-}hC_{\gamma 1}$ | $(mV_\kappa C_\kappa)_2(hCD4\text{-}hC_{\gamma 1})_2 +$ $mV_\kappa C_\kappa$ and/or $(mV_\kappa C_\kappa)_2$ |

CD4-IgG hybrids (chimeras) are readily secreted wherein the CD4 epitope is present in heavy chain dimers, light chain monomers or dimers, and heavy and light chain heterotetramers wherein the CD4 epitope is present fused to one or more light or heavy chains, including heterotetramers wherein up to and including all four variable region analogues are derived from CD4. Where a light and/or heavy chain non-CD4 variable domain is present, a heterofunctional antibody thus is provided. Typically, a heavy-light chain heterodimer capable of binding a predetermined antigen is disulfide bonded in the ordinary fashion through the heavy chain constant domain to a CD4-heavy chain chimera. The predetermined antigen can be a platelet antigen or a viral (e.g. HIV) antigen.

The preparation of the particular CD4-IgG-1 hybrid used in our clinical trials is described in the Example. The term "(human) rCD4-IgG-1" as used throughout the specification and claims refers to this specific hybrid.

In general, the hybrid molecules used in accordance with the present invention are constructed in a fashion similar to chimeric antibodies in which a variable domain from an antibody of one species is substituted for the variable domain of another species. See, for example, EP 0 125 023; Munro, *Nature* 312: (13 Dec. 1984); Neuberger et al., *Nature* 312: (13 Dec. 1984); Sharon et al., *Nature* 309: (24 May 1984); Morrison et al., *Proc. Nat'l. Acad. Sci. USA* 81:6851–6855 (1984); Morrison et al. *Science* 229:1202–1207 (1985); and Boulianne et al., *Nature* 312:643–646 (13 Dec. 1984). The DNA encoding the desired CD4 immunoglobulin-like domain(s) is cleaved by a restriction enzyme at or proximal to the 3' end of the DNA encoding the immunoglobulin-like domain(s) and at a point at or near the DNA encoding the N-terminal end of the mature CD4 polypeptide (where use of a different leader is contemplated) or at or proximal to the N-terminal coding region for CD4 (where the native signal is employed). This DNA fragment then is readily inserted proximal to DNA encoding an immunoglobulin light or heavy chain constant region and, if necessary, the resulting construct tailored by deletional mutagenesis. Preferably, the Ig is a human immunoglobulin when the variant is intended for in vivo therapy for humans. DNA encoding immunoglobulin light or heavy chain constant regions is known or readily available from cDNA libraries or is synthesized. See for example, Adams et al., *Biochemistry* 19:2711–2719 (1980); Gough et al., *Biochemistry* 19:2702–2710 (1980); Dolby et al., *P.N.A.S. USA*, 77:6027–6031 (1980); Rice et al., *P.N.A.S. USA* 79:7862–7865 (1982); Falkner et al., *Nature* 298:286–288 (1982); and Morrison et al., *Ann. Rev. Immunol.* 2:239–256 (1984).

According to an another embodiment of the present invention, HIV-associated ITP is treated with a molecule comprising an immunoglobulin variable region. Antibodies (specific immunglobulin polypeptides with specificity for an HIV antigen), and specifically monoclonal antibodies to gp120, are particularly suitable for this purpose. As used herein, the term "antibodies" refers to teramers or aggregates thereof which have specific immunoreactive activity, comprising light and heavy chains usually aggregated in an "Y" configuration, with or without covalent linkage between them; whereas the term "immunoglobulins" refers to such assemblies whether or not specific immunoreactive activity is a property.

Methods for the production of monoclonal antibodies are well known in the art [Kohler et al. [*Eur. J. Immunol.* 6, 511 (1976); Current Protocols in Molecular Biology, Ausubel, F. M. et al. Eds., Greene Publishing Associates and Wiley-Interscience, 1988, Vol. 2]. In this process, splenocytes or lymphocytes from a mammal injected with an antigen are fused with a tumor cell line, to yield hybridomas which are both immortal and capable of producing the genetically coded antibody of the B cell. The hybrids are segregated into single genetic strains by selection, dilution, and regrowth, and each strain thus represents a single genetic line. They therefore produce immunoreactive antibodies against a desired antigen which are assured to be homogenous, and which antibodies, referencing their pure genetic parentage, and called "monoclonal". Alternatively, antibodies can be produced by using techniques of recombinant DNA technology. Recombinant techniques are suitable for producing antibodies which are analogous to those normally found in vertebrate systems, and also for constructing chimeric or other modified forms, specifically designed for a particular application [see, e.g. U.S. Pat. No. 4,816,567 and the references cited hereinabove for the construction of chimeric antibodies]. Recombinant techniques can, for example, produce antibodies with a CD4 domain, structurally analogous to the CD4-immunoglobulin hybrids discussed hereinabove. The use of such recombinant antibodies for the treatment of HIV-associated ITP is within the scope of the present invention.

The compounds of the present invention are administered in the form of conventional pharmaceutical formulations, in association with non-toxic, pharmaceutically acceptable ingredients. Such formulations can be prepared by known methods described, for example, in Remington's Pharmaceutical Sciences, 16th Ed. 1980, Mac Publishing Company, which is hereby specifically incorporated by reference, and are typically administered parenterally by injection. Whereas intravenous, intraperitoneal, intramuscular and subcutaneous routes of administration are possible, the intravenous route is preferred.

The molecules comprising an amino acid sequence capable of binding to HIV are administered in a therapeutically effective amount. The term "therapeutically effective amount" is used to define an amount resulting in the improvement of any parameters or clinical symptoms characteristic of the condition of ITP, including bleeding symptoms and platelet count depression. A positive change in such parameters or symptoms, e.g. an increase in platelet count or the moderation or elimination of bleeding symptoms are considered a positive response. If the monitoring is based on the evaluation of the platelet counts, "complete response" is defined as the increase of the platelet count to at least 150,000 cells/mm$^3$ whereas "partial response" refers to a platelet count less than 150,000 cells/mm$^3$ and a greater than or equal to 30,000 cells/mm$^3$ increase from baseline (i.e. the platelet count prior to treatment). However, other (or additional) methods, such as the detection of platelet-associated immunoglobulin by fluorescence-activated flow cytometric assay, bone marrow examination, platelet survival can also be used for monitoring the response of the ITP patients to therapy.

The actual dose will be different for the various specific molecules, and will vary with the patient's overall condition, the seriousness of the symptoms, counterindications, etc. The determination of the effective dose is well within the skill of a practicing physician. For the CD4-Ig conjugates the daily dosage is typically higher than about 1 mg/kg of body weight, and preferably is in the range of about 1 and about 20 mg/kg of body weight, more preferably between about 1 and about 10 mg/kg of body weight. Compounds comprising a CD4 sequence not linked to an immunoglobulin sequence are administered in higher doses, and more frequently due to the short half-life and rapid clearance of CD4.

Further details of the invention are illustrated in the following non-limiting Example.

EXAMPLE

Study of the effect of recombinant human CD4-Immunoglobulin G-1 (rCD4-IgG-1) on HIV-associated ITP

Materials and Methods

The rCD4-IgG-1 hybrid used in this study was a homodimer of a hybrid polypeptide consisting of residues 1–180 of the mature human CD4 protein fused to human IgG-1 sequences beginning at aspartic acid 216 (taking amino acid 114 as the first residue of the heavy chain constant region [Kabat et al., Supra]) which is the first residue of the IgG-1 hinge after the cysteine residue involved in heavy-light chain bonding, and ending with residue 441. This antibody-like molecule, the structure of which is illustrated in FIG. 1, contains two N-terminal CD4 domains, a hinge region and the $C_H2$ and $C_H3$ Fc domains. The $C_H2$ domain contains the only potential N-linked glycosylation site on the molecule. The CD4-IgG-1 hybrid shown in FIG. 1, which lacks the CH1 domain, was derived from a CH1-containing CD4-IgG-1 hybrid (immunoadhesin) the preparation of which was described by Capon et al., *Nature* 337,525–531 (1989) and is disclosed in the PCT Patent Application Publication No. WO 89/02922 (published 6 Apr. 1989) claiming the priorities of U.S. Ser. No.07/104,329 (filed 20 Oct. 1987) and U.S. Ser. No. 07/250,785 (filed 28 Sep. 1988), the contents of which are expressly incorporated by reference. The present (CH1-lacking) hybrid was obtained by oligonucleotide-directed deletional mutagenesis [Zoller, M. & Smith, M., *Nucleic Acids Res.* 10, 6487–6500 (1982)], and expressed in Chinese hamster ovary (CHO) cells after their insertion into a mammalian expression vector used for soluble rCD4 expression [Smith et al., *Science* 238, 1704–1707 (1987)]. The product was purified to a purity exceeding 99% using protein A-Sepharose chromatography, as described by Capon et al., Supra.

To prepare a pharmaceutical formulation, the rCD4-IgG-1 hybrid was diluted with sufficient formulation buffer to produce a 5.0 mg/ml concentration of rCD4-IgG. The formulation buffer consisted of 0.16 mg/ml citric acid monohydrate, 2.7 mg/ml trisodium citrate, 41 mg/ml mannitol, 1 mg/ml glycine and 1 mg/ml polysorbate 20. The solution obtained was lyophilized, and the lyophilized powder was filled into vials with a nominal content of 5 mg and 25 mg rCD4-IgG-1, which were stored under refrigeration. Immediately before administration, the 5 mg and 25 mg vials of rCD4-IgG-1 were reconstituted with 1.2 ml and 5.5 ml of Serile Water-for-Injection, USP, respectively, to result in a concentration of 5 mg/ml.

Study Design

The safety and efficacy of rCD4-IgG-1 in patients with HIV-associated thrombocytopenic purpura (ITP) were studied. The study has been performed on male and female subjects, 18 years or older. Patients were selected to meet the following criteria:

1. Patients were required to have a platelet count of 100,000/mm³ or less on two successive occasions done one week apart. Patients with platelet count≦10,000/mm³ were excluded from the study.

2. Previously documented HIV-1 seropositivity.

a. Patients with AIDS (using the diagnostic criteria of the Centers for Disease Control) must have had no more than 2 prior episodes of pneumocystis carinii pneumonia, and no more than one prior episode of another serious opportunistic infection.

b. Patients with HIV infection without a diagnosis of AIDS and not asymptomatic: They must have had a history of one of the following symptoms: thrush, oral hairy leukoplakia, fevers, night sweats, weight loss, diarrhea, fatigue, dermatitis.

c. Asymptomatic patients.

The enrolled patients had otherwise normal hepatic, hematologic, coagulation and renal function. Patients previously treated with zidovidine were allowed to remain on this treatment. Subjects with active serious opportunistic infections, significant neurologic, cardiac or liver disease were excluded from this study.

Post study evaluation was performed within 3–7 days of the completion of the study or withdrawal from treatment. The response criteria were as follows:

1. Complete response was a platelet count of at least 150,000 cells/mm³.

2. Partial response was a platelet count less than 150,000 cells/mm³ and a greater than or equal to 30,000 cells/mm³ increase from baseline.

3. No response was less than a 30,000 cells/m³ increase from baseline.

After completion of the initial 8-week phase of the protocol, patients who responded to the treatment and showed no evidence of toxicity were allowed to stay on maintenance therapy. Maintenance therapy is initiated within 2 weeks of completion of the initial 8 weeks of study and involves the administration of a 75 mg per infusion unit dose of rCD4-IgG two times a week.

Clinical and Laboratory Monitoring

At entry and throughout the study, subjects were evaluated clinically with interval histories, vital signs, and physical examinations. Safety monitoring by laboratory evaluation at regularly scheduled intervals included complete blood count with differential, platelet count, and reticulocyte count, chemistry profile, including albumin, alkaline phosphatase, total bilirubin, blood urea nitrogen, calcium, cholesterol, triglycerides, glucose, lactate dehydrogenase, aspartate aminotransferase, alanine aminotransferase, sodium, potassium, and uric acid; routine urine analysis; coagulation profile; chest radiograph; and electrocardiogram, and (for female patients) pregnancy test.

Results

Figure 2:
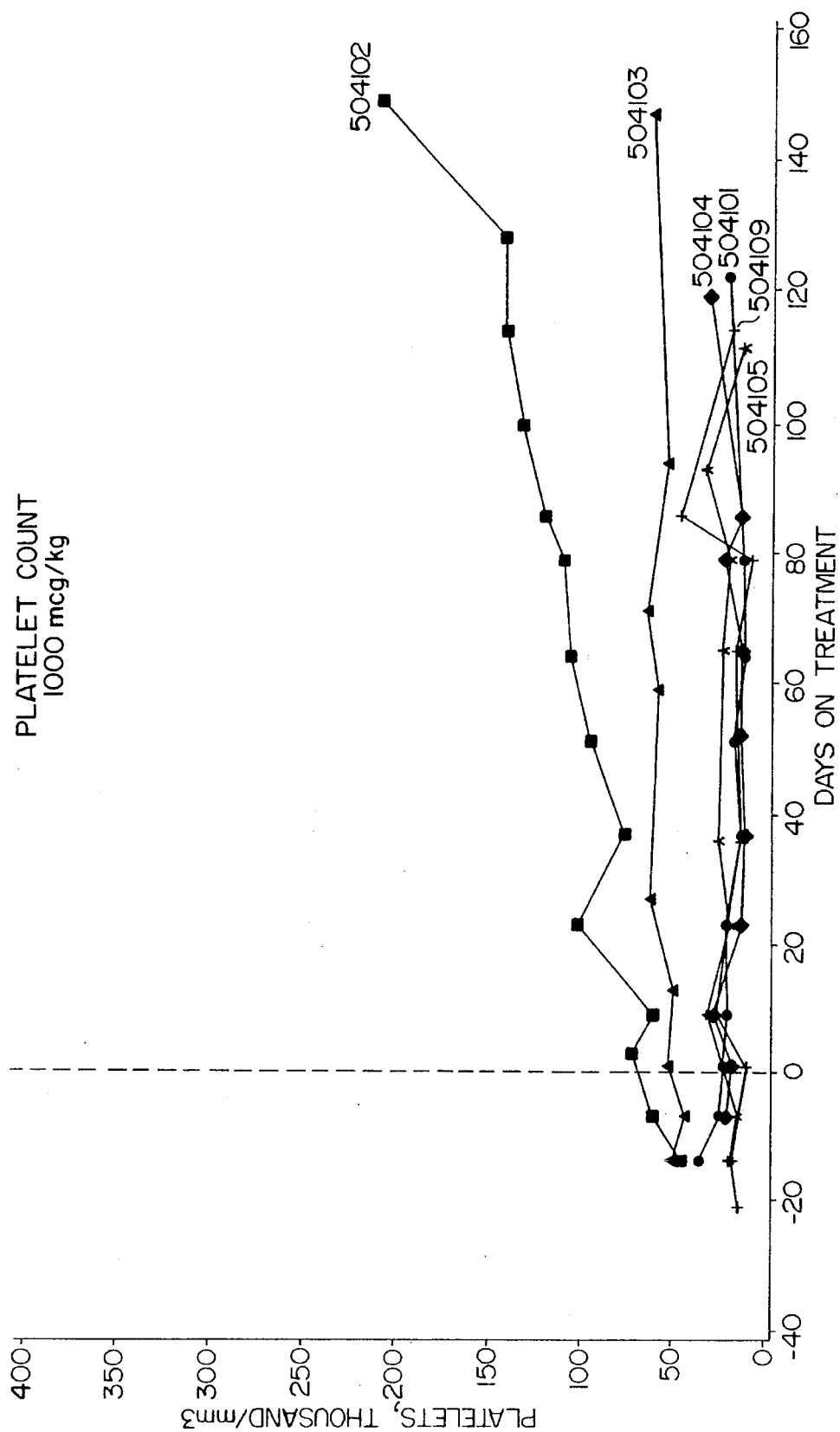
FIGS. 2 and 3 are graphical illustrations of the results recorded in two series of clinical trials. The platelet counts are shown as a function of the time of treatment.

FIG. 2 illustrates the results obtained on six subjects treated with rCD4-IgG-1 at a fixed dose level of 1 mg/kg by intravenous bolus injection on days 1 through 7, followed by intravenous boluses two times per week for the indicated time. One patient had a partial response with platelet counts above 100,000. rCD4-IgG-1 was well tolerated by all subjects with insignificant clinical toxicity.

Figure 3:
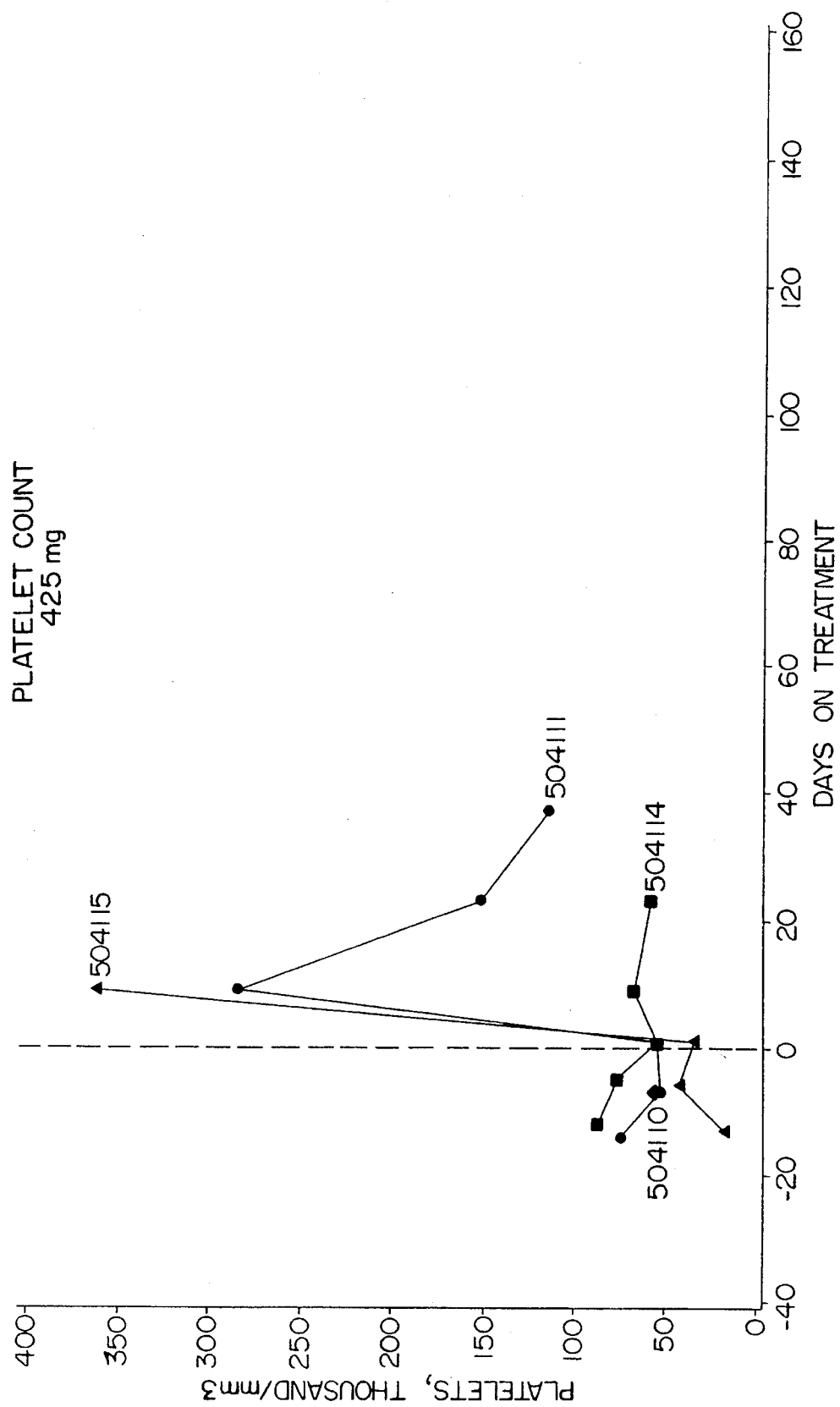

FIG. 3 illustrates the results of another series of tests, where four subjects were treated at a fixed dose level of 6 mg/kg, under otherwise similar conditions. Of the patients reported in FIG. 3, two patients' platelet counts increased to at least $220 \times 10^9$ cells per liter by two weeks (complete response) and one subject showed no response.

All citations cited throughout the specification, and the references cited therein, are hereby expressly incorporated by reference.

Although the foregoing refers to particular preferred embodiments, it will be understood that the present invention is not so limited. It will occur to those ordinarily skilled in the art that various modifications may be made to the disclosed embodiments without diverting from the overall concept of the invention. All such modifications are intended to be within the scope of the present invention.

I claim:

1. A method for the treatment of human immunodeficiency virus associated immune thrombocytopenic purpura which comprises:

a) administering to a patient having the condition of human immunodeficiency virus-associated immune thrombocytopenic purpura about 6 mg/ml of a hybrid molecule consisting essentially of the V1 and V2 domains of CD4 fused at the carboxy terminus to the N-terminus of an IgG heavy chain constant region consisting essentially of a hinge and the CH2 and CH3 domains;

b) monitoring the change in a parameter or symptom characteristic of the condition of human immunodeficiency virus-associated immune thrombocytopenic purpura in response to the administration; and c) continuing the treatment until a positive response is attained.

2. The method of claim 1 wherein said parameter is the platelet count.

3. The method of claim 2 wherein the platelet count of the patient prior to treatment is between about $100 \times 10^9$ platelets per liter and about $10 \times 10^9$ per liter.

4. The method of claim 3 wherein the criteria for positive response is a platelet count of at least $150 \times 10^9$ cells/liter or an at least $30 \times 10^9$ cells/liter increase from the platelet count prior to treatment.

5. The method of claim 1 wherein the IgG heavy chain constant region is obtained from IgG-1, -2, -3, or -4 subtypes.

6. The method of claim 5 wherein the IgG heavy chain constant region is obtained from IgG-1.

7. The method of claim 6 wherein said molecule is human rCD4-IgG-1.

* * * * *